United States Patent
Leschinsky et al.

(10) Patent No.: US 6,245,008 B1
(45) Date of Patent: Jun. 12, 2001

(54) FAST RESPONSE INTRA-AORTIC BALLOON PUMP

(75) Inventors: Boris Leschinsky, Waldwick; Jonathan R. Williams, Montville, both of NJ (US)

(73) Assignee: Datascope Investment Corporation, Montvale, NJ (US)

( * ) Notice: Subject to any disclaimer, the term of this patent is extended or adjusted under 35 U.S.C. 154(b) by 0 days.

(21) Appl. No.: 09/678,698

(22) Filed: Oct. 3, 2000

Related U.S. Application Data

(62) Division of application No. 09/356,096, filed on Jul. 16, 1999.

(51) Int. Cl.⁷ .................................................. A61N 1/362
(52) U.S. Cl. ........................................ 600/18; 604/99.01
(58) Field of Search ............................. 600/18, 495–496; 606/192–195; 623/3.1, 26; 604/99.01, 99.02, 99.03, 99.04, 96

(56) References Cited

U.S. PATENT DOCUMENTS

| | | |
|---|---|---|
| 4,794,910 | 1/1989 | Mushika .................................. 600/18 |
| 4,796,606 | 1/1989 | Mushika .................................. 600/18 |
| 4,832,005 | 5/1989 | Takamiya et al. ...................... 600/18 |
| 4,974,774 | 12/1990 | Nakagawa et al. ..................... 600/18 |
| 5,158,529 | 10/1992 | Kanai ..................................... 600/18 |
| 5,169,379 | 12/1992 | Freed et al. ............................. 600/18 |
| 5,759,148 | 6/1998 | Sipin ....................................... 600/18 |
| 5,817,001 | 10/1998 | Leschinsky et al. ................... 600/18 |
| 5,885,244 | 3/1999 | Leone et al. ............................ 604/96 |
| 5,913,814 | 5/1999 | Zantos .................................... 600/18 |

*Primary Examiner*—Manuel Mendez
(74) *Attorney, Agent, or Firm*—Lerner, David, Littenberg, Krumholz & Mentlik, LLP

(57) ABSTRACT

An intra-aortic balloon pump includes a balloon, a catheter having a relatively small diameter lumen and an extender having a relatively large diameter lumen connected in series. A valve is positioned in the extender adjacent the end of the extender connected to the catheter. The valve enables the extender to be pressurized with a working gas prior to inflation of the balloon and to be evacuated prior to deflation of the balloon. A second valve adjacent the opposite end of the extender permits the intra-aortic balloon pump to commence a pre-inflation step or a pre-deflation step without affecting the pressure in the extender. Separate positive pressure and negative pressure extenders may be provided to reduce the movement of the working gas during inflation and deflation cycles, thereby increasing pneumatic efficiency.

22 Claims, 8 Drawing Sheets

FAST RESPONSE INTRA-AORTIC BALLOON PUMP

CROSS REFERENCE TO PRIOR APPLICATION

This application is a divisional of U.S. application Ser. No. 09/356,096 filed Jul. 16, 1999, the disclosure of which is hereby incorporated by reference herein.

FIELD OF THE INVENTION

The present invention relates generally to intra-aortic balloon pumps, and more particularly, to systems for inflating and deflating intra-aortic balloons. Still more particularly, the present invention relates to such a system incorporating one or more strategically placed valves enabling more rapid inflation and deflation of the intra-aortic balloon.

BACKGROUND OF THE INVENTION

Intra-aortic balloon pump therapy is frequently prescribed for patients who have suffered a heart attack or some other form of heart failure. In such therapy, a thin balloon is inserted through an artery into the patient's aorta. The balloon is connected through a series of tubes to a complex drive apparatus which causes the balloon to inflate and deflate repeatedly in time with the patient's heartbeat, thereby removing some of the load from the heart and increasing blood supply to the heart muscle during the therapy period.

The inflation/deflation apparatus supplies positive pressure for expanding the balloon during an inflation cycle and negative pressure for contracting the balloon during a deflation cycle. In a conventional prior art apparatus shown schematically in FIG. 1, an intra-aortic balloon 10 is surgically inserted into a patient's aorta and is connected through a catheter 12 having a small diameter lumen and an extender 14 having a relatively large diameter lumen to an isolator 18 divided by a pliant membrane 20 into a primary side 22 and a secondary side 24. The entire volume between membrane 20 and balloon 10 is completely filled with a gas, such as helium, supplied by a gas source 26. A positive pressure source 28 is connected through a solenoid valve 30 to the input or primary side 22 of isolator 18. Similarly, a negative pressure source 32 is connected through a solenoid valve 34 to the input or primary side 22 of isolator 18. The primary side 22 of isolator 18 is also connected through a solenoid valve 36 to a vent or exhaust port 38. Typically in such systems, the isolator, gas source, negative and positive pressure sources, vent port and their associated valves together comprise a reusable drive unit, and the extender, catheter and balloon are disposable so as to accommodate sterility concerns.

During an inflation cycle, solenoid valve 30 is opened to permit positive pressure from positive pressure source 28 to enter primary side 22 of isolator 18. This positive pressure causes membrane 20 to move toward secondary side 24, thereby forcing the helium in the secondary side to travel toward and inflate balloon 10. For deflation, solenoid valve 30 is closed and solenoid valve 36 is opened briefly to vent the gas from primary side 22, after which valve 36 is closed. Solenoid valve 34 is then opened, whereupon negative pressure source 32 creates a negative pressure on the primary side 22 of isolator 18. This negative pressure pulls membrane 20 toward primary side 22, whereby the helium is drawn out from the balloon.

It is desirable in intra-aortic balloon pump therapy to inflate and deflate the balloon as rapidly as possible. Rapid cycling would permit the therapy to be performed more effectively, and would enable smaller diameter catheters to be used, thereby reducing the possibility of limb ischemia. Although the prior art system described above permits rapid inflation and deflation cycles, the configuration of this system creates inherent limitations in the cycle speed which can be achieved.

Thus, in a typical inflation cycle, pressurized gas from positive pressure source 28, at an initial pressure of about 8 psi, is used to inflate balloon 10 to an end inflation pressure of about 2 psi, which is about the blood pressure of a normal patient. (In the present specification, all references to psi, unless otherwise noted, are to gauge pressures, not absolute pressures.) In the initial portion of the inflation cycle, the 8 psi gas pressure on the primary side 22 of isolator 18 drives membrane 20 toward the secondary side 24, forcing the gas in secondary side 24 into extender 14. Because of its small diameter, however, catheter 12 acts as a constriction to the rapid flow of gas to balloon 10. Hence, when membrane 20 has moved fully forward (i.e., it hits the wall on secondary side 24), there is a relatively large pressure differential across catheter 12, and balloon 10 is only partially inflated. The process of balloon inflation continues as the gas in extender 14 flows through catheter 12 to the balloon until a state of equilibrium is reached in the closed portion of the system. It is therefore apparent that the pressure differential across catheter 12 is highest at the beginning of the inflation cycle and drops to zero at the end of the inflation cycle. Since the rate at which gas flows from extender 14 to balloon 10 is dependent upon the pressure differential across catheter 12, this gradual decay in the pressure differential results in a steadily decreasing flow rate and, therefore, a longer overall time until equilibrium is reached and the balloon is fully inflated.

A similar situation occurs during the deflation portion of the cycle. Thus, as the deflation cycle begins, a large negative pressure is created on primary side 22 of isolator 18 by negative pressure source 32. This negative pressure pulls membrane 20 toward primary side 22, whereupon the gas in extender 14 is drawn into the secondary side 24 of the isolator. Again, the small diameter of catheter 12 constricts the flow of gas out from balloon 10 such that, with membrane 20 moved to its fully retracted position (i.e., against the wall on primary side 22), a relatively large pressure differential exists across catheter 12, and balloon 10 is only partially deflated. As helium flows slowly from balloon 10 through catheter 12, the balloon continues to deflate until equilibrium is reached. Here again, the pressure differential across catheter 12 which drives balloon deflation is at its highest at the beginning of the deflation cycle and drops to zero at the end of the cycle. The gradual decrease in the pressure differential results in a steadily decreasing flow rate across catheter 12, lengthening the overall time until the balloon is fully deflated.

At first blush, it would appear that more rapid inflation/deflation cycles can be achieved simply by using a higher positive pressure during inflation and a lower negative pressure during deflation. The use of a higher positive pressure, however, creates the risk of overinflating and stressing the balloon, with the attendant risk of aneurization or rupturing of the balloon. Alternatively, simply increasing the volume of the isolator so that the maximum pressure differential across catheter 12 would be maintained for a longer period of time before membrane 20 has bottomed out would, without other modification to the system, create problems. Not only would there be a risk of damaging the balloon through overinflation, there would also be a need to remove a larger amount of gas from the balloon during deflation, which requirement would increase the deflation time.

There are generally three aspects of the operation of intra-aortic balloon pumps which contribute to inflation/deflation cycle times—the time required to deliver electrical signals from the controller to the various valves; the time required to effect the mechanical operations, i.e., movement of the isolator membrane and actuation of the valves between open and closed positions; and the time required to move the gas, either between the positive and negative pressure sources and the isolator on the primary side, or between the balloon and the isolator on the secondary side. By reducing the time needed to perform any one of these operations, more rapid inflation/deflation cycles may be achieved.

One approach for increasing inflation and deflation speeds by reducing gas movement time is shown schematically in FIG. 2 and described in U.S. Pat. Nos. 4,794,910; 4,796,606; 4,832,005; 5,158,529 and 5,169,379. In this approach, a valve 25 is positioned between the secondary side 24 of isolator 18 and extender 14 so as to separate the reusable drive unit from the disposable components. Valve 25 isolates the balloon 10, catheter 12 and extender 14 from isolator 18, thereby enabling the secondary side 24 of isolator 18 to be pressurized before balloon 10 needs to be inflated, and to be depressurized before balloon 10 needs to be deflated.

In the operation of the system of FIG. 2, an inflation cycle is initiated by closing valve 25 and opening valve 30, causing membrane 20 to move toward and pressurize secondary side 24 of isolator 18. Since valve 25 is closed, no helium flows toward balloon 10 which remains in a deflated state. When inflation is required, valve 25 is opened, causing the pressurized helium in secondary side 24 to flow through extender 14 and catheter 12 to inflate balloon 10. Since secondary side 24 of isolator 18 is already pressurized at the time valve 25 is opened, inflation of balloon 10 occurs more rapidly than with the system of FIG. 1 in which secondary side 24 must first be pressurized when inflation is called for. Once balloon 10 has been inflated, valves 25 and 30 may be closed and valve 36 briefly opened to vent the gas from primary side 22, after which valve 36 is closed. With valve 25 still closed, valve 34 may be opened, whereupon a negative pressure is created in primary side 22, pulling membrane 20 toward primary side 22 and creating a negative pressure in secondary side 24. When deflation is desired, valve 25 may be opened, whereupon the helium is drawn out from the balloon. Since a negative pressure already exists on secondary side 24 of isolator 18 when the deflation cycle begins, balloon 10 deflates more rapidly than with the system of FIG. 1 in which a negative pressure must first be developed in secondary side 24 when deflation is called for.

Despite the more rapid inflation/deflation cycles attainable with the system of FIG. 2, still more improvements in cycle speeds are desirable. Faster inflation and deflation cycles would provide operational benefits, including improved operational reliability at high heart rates, increased augmentation of patient blood pressure, and improved tracking of the patient's heart activity in cases of arrhythmia. These improvements in response times preferably will be obtainable without the use of higher magnitude operating pressures and the risks of leakage and balloon failure attendant therewith.

SUMMARY OF THE INVENTION

The present invention addresses these needs.

One aspect of the present invention provides a method for inflating and deflating a medical device, the medical device being connected to a conduit including a tubular extender portion having a relatively large diameter lumen and a tubular catheter portion having a relatively small diameter lumen connected in series so that one end of the catheter portion is connected in flow communication to one end of the extender portion and another end of the catheter portion is connected in flow communication to the medical device.

In one embodiment according to this aspect of the present invention, the method may be used during the inflation phase of an inflation/deflation cycle. In accordance with this method, a working gas is applied to the extender portion to develop an inflation pressure therein while flow communication between the extender portion and the catheter portion is interrupted, whereby the working gas is prevented from flowing into the catheter portion and the medical device. Flow communication is then established between the extender portion and the catheter portion, whereby the working gas flows from the extender portion through the catheter portion to the medical device to substantially fully inflate the medical device to a working pressure lower than the inflation pressure. Subsequently, the pressure in the extender portion may be reduced to a deflation pressure less than the working pressure, whereby the working gas flows from the medical device through the catheter portion to the extender portion to substantially fully deflate the medical device.

In another embodiment according to this aspect of the present invention, the method may be used during the deflation phase of an inflation/deflation cycle. In accordance with this method, a working gas is applied to the extender portion to develop an inflation pressure therein, whereby the working gas flows from the extender portion through the catheter portion to the medical device to substantially fully inflate the medical device to a working pressure. The working gas is then removed from the extender portion to develop a deflation pressure therein while flow communication between the extender portion and the catheter portion is interrupted, whereby the working gas is prevented from flowing out from the catheter portion and the medical device, the deflation pressure being less than the working pressure. Flow communication is then established between the extender portion and the catheter portion, whereby the working gas flows from the medical device through the catheter portion to the extender portion to substantially fully deflate the medical device.

In yet another embodiment hereof, the method of the present invention may be used during both the inflation and deflation portions of the cycle. Such method may further include the step of providing a hollow element at a free end of the extender portion, and the step of applying the working gas to the extender portion may include the steps of supplying the working gas to the hollow element at a pressure greater than the pressure prevailing in the extender portion, and establishing a first flow communication between the hollow element and the extender portion, whereby the working gas flows from the hollow element into the extender portion. Preferably, the first flow communication between the hollow element and the extender portion is established after the working gas is supplied to the hollow element. In preferred embodiments hereof, the step of removing the working gas from the extender portion may include the steps of supplying the working gas to the hollow element at a pressure less than the working pressure, and establishing a second flow communication between the hollow element and the extender portion, whereby the working gas flows from the extender portion into the hollow element. Preferably, the second flow communication between the hollow element and the extender portion is established after the working gas is supplied to the hollow element at a pressure less than the working pressure.

In a variant of this embodiment, the first flow communication between the extender portion and the catheter portion may be established while there is flow communication between the hollow element and the extender portion. This variant may further include the steps of interrupting the first flow communication between the hollow element and the extender portion while there is flow communication between the extender portion and the catheter portion, and supplying the working gas to the hollow element at a pressure less than the working pressure. The step of removing the working gas from the extender portion may include the step of establishing a second flow communication between the hollow element and the extender portion, whereby the working gas flows from the extender portion into the hollow element.

In another variant of this embodiment, the first flow communication between the hollow element and the extender portion may be interrupted after the inflation pressure has been developed in the extender portion and prior to the step of establishing the first flow communication between the extender portion and the catheter portion. In accordance with this variant, the working gas may be supplied to the hollow element at a pressure less than the working pressure after the first flow communication between the hollow element and the extender portion has been interrupted, whereupon the working gas will not flow from the extender portion to the hollow element. The working gas may then be removed from the extender portion by establishing a second flow communication between the hollow element and the extender portion. This variant may further include the step of interrupting the second flow communication between the hollow element and the extender portion after the deflation pressure has been developed in the extender portion and prior to the step of establishing the second flow communication between the extender portion and the catheter portion.

In a further variant hereof, a variable volume reservoir may be provided in flow communication with the extender portion, wherein the step of applying the working gas to the extender portion develops the inflation pressure in both the variable volume reservoir and the extender portion. Preferably, when the first flow communication is established between the extender portion and the catheter portion and the working gas flows from the extender portion through the catheter portion to the medical device, the working gas will flow from the variable volume reservoir to the extender portion. More preferably, the step of removing the working gas from the extender portion will develop the deflation pressure in both the variable volume reservoir and the extender portion. When the second flow communication is established between the extender portion and the catheter portion and the working gas flows from the medical device through the catheter portion to the extender portion, the working gas preferably flows from the extender portion to the variable volume reservoir.

In yet another variant of this embodiment, a variable volume reservoir may be provided in flow communication with the extender portion, wherein the step of removing the working gas from the extender portion develops the deflation pressure in both the variable volume reservoir and the extender portion. Preferably, when the second flow communication is established between the extender portion and the catheter portion and the working gas flows from the medical device through the catheter portion to the extender portion, the working gas flows from the extender portion to the variable volume reservoir.

In yet a further embodiment according to this aspect of the present invention, a hollow element may be provided at a free end of the extender portion, and the step of removing the working gas from the extender portion may include the steps of supplying the working gas to the hollow element at a pressure less than the working pressure, and establishing flow communication between the hollow element and the extender portion, whereby the working gas flows from the extender portion into the hollow element. Preferably, the second flow communication between the extender portion and the catheter portion is established while there is flow communication between the hollow element and the extender portion.

Another aspect of the present invention provides a method for inflating and deflating a medical device, the medical device being connected to a conduit including a tubular inflation extender portion having a relatively large diameter lumen, a tubular deflation extender portion having a relatively large diameter lumen, and a tubular catheter portion having a relatively small diameter lumen, the catheter portion and the medical device being connected in series with the inflation and deflation extender portions so that one end of the catheter portion is connected in flow communication both to one end of the inflation extender portion and to one end of the deflation extender portion and another end of the catheter portion is connected in flow communication to the medical device.

In one embodiment according to this aspect of the present invention, the method may be used during the inflation phase of an inflation/deflation cycle. In accordance with this method, a working gas is applied to the inflation extender portion to develop an inflation pressure therein while flow communication between the inflation extender portion and the catheter portion is interrupted, whereby the working gas is prevented from flowing into the catheter portion and the medical device. Flow communication is then established between the inflation extender portion and the catheter portion while flow communication between the deflation extender portion and the catheter portion is interrupted, whereby the working gas flows from the inflation extender portion through the catheter portion to the medical device to substantially fully inflate the medical device to a working pressure lower than the inflation pressure. A deflation pressure less than the working pressure is established in the deflation extender portion and flow communication is established between the deflation extender portion and the catheter portion while flow communication between the inflation extender portion and the catheter portion is interrupted, whereby the working gas flows from the medical device through the catheter portion to the deflation extender portion to substantially fully deflate the medical device.

In another embodiment according to this aspect of the present invention, the method may be used during the deflation phase of an inflation/deflation cycle. In accordance with this method, a working gas is applied to the inflation extender portion to develop an inflation pressure therein, whereby the working gas flows from the inflation extender portion through the catheter portion to the medical device to substantially fully inflate the medical device to a working pressure. The working gas is applied to the deflation extender portion to develop a deflation pressure therein while flow communication between the deflation extender portion and the catheter portion is interrupted, whereby the working gas is prevented from flowing out from the catheter portion and the medical device, the deflation pressure being less than the working pressure. Flow communication is then established between the deflation extender portion and the catheter portion while flow communication between the inflation extender portion and the catheter portion is interrupted, whereby the working gas flows from the medical device through the catheter portion to the deflation extender portion to substantially fully deflate the medical device.

In a still further embodiment hereof, the method of the present invention may be used during both the inflation and deflation portions of the cycle. Such method may further include the step of providing a hollow inflation element at a free end of the inflation extender portion, and the step of applying the working gas to the inflation extender portion may include the steps of supplying the working gas to the hollow inflation element at a pressure greater than the pressure prevailing in the inflation extender portion, and establishing flow communication between the hollow inflation element and the inflation extender portion, whereby the working gas flows from the hollow inflation element into the inflation extender portion. Preferred embodiments of such method may further include the step of providing a hollow deflation element at a free end of the deflation extender portion, and the step of applying the working gas to the deflation extender portion may include the steps of supplying the working gas to the hollow deflation element at a pressure less than the working pressure, and establishing flow communication between the hollow deflation element and the deflation extender portion, whereby the working gas flows from the deflation extender portion into the hollow deflation element. The hollow deflation element may be the same as the hollow inflation element.

In highly preferred methods, a hollow element may be provided at both a free end of the inflation extender portion and a free end of the deflation extender portion. In accordance with such methods, the step of applying the working gas to the inflation extender portion may include the steps of supplying the working gas to the hollow element at a pressure greater than the pressure prevailing in the inflation extender portion, and establishing flow communication between the hollow element and the inflation extender portion, whereby the working gas flows from the hollow element into the inflation extender portion. Also in accordance with such methods, the step of applying the working gas to the deflation extender portion may include the steps of supplying the working gas to the hollow element at a pressure less than the working pressure, and establishing flow communication between the hollow element and the deflation extender portion, whereby the working gas flows from the deflation extender portion into the hollow element.

Preferably, the flow communication between the inflation extender portion and the catheter portion is established while there is flow communication between the hollow element and the inflation extender portion. Preferred methods may further include the steps of interrupting flow communication between the hollow element and the inflation extender portion while there is flow communication between the inflation extender portion and the catheter portion, and supplying the working gas to the hollow element at a pressure less than the working pressure. In more preferred methods, the step of applying the working gas to the deflation extender portion may include the step of establishing flow communication between the hollow element and the deflation extender portion, whereby the working gas flows from the deflation extender portion into the hollow element.

Another method in accordance with this embodiment of the invention may further include the step of interrupting flow communication between the hollow element and the inflation extender portion after the inflation pressure has been developed in the inflation extender portion and prior to the step of establishing flow communication between the inflation extender portion and the catheter portion. The working gas may be supplied to the hollow element at a pressure less than the working pressure after flow communication between the hollow element and the inflation extender portion has been interrupted, whereby the working gas does not flow from the inflation extender portion to the hollow element. Preferably, the step of supplying the working gas to the deflation extender portion includes the step of establishing flow communication between the hollow element and the deflation extender portion. Preferred embodiments may further include the step of interrupting flow communication between the hollow element and the deflation extender portion after the deflation pressure has been developed in the deflation extender portion and prior to the step of establishing flow communication between the deflation extender portion and the catheter portion.

In a variant of the foregoing embodiments, a variable volume inflation reservoir may be provided in flow communication with the inflation extender portion, wherein the step of applying the working gas to the inflation extender portion develops the inflation pressure in both the variable volume inflation reservoir and the inflation extender portion. Preferably, when flow communication is established between the inflation extender portion and the catheter portion and the working gas flows from the inflation extender portion through the catheter portion to the medical device, the working gas flows from the variable volume inflation reservoir to the inflation extender portion.

In another variant, a variable volume deflation reservoir may be provided in flow communication with the deflation extender portion, wherein the step of applying the working gas to the deflation extender portion develops the deflation pressure in both the variable volume deflation reservoir and the deflation extender portion. When flow communication is established between the deflation extender portion and the catheter portion and the working gas flows from the medical device through the catheter portion to the deflation extender portion, the working gas preferably flows from the deflation extender portion to the variable volume deflation reservoir.

A still further aspect of the present invention provides a medical apparatus including an inflatable member having an inflated condition and a deflated condition; a catheter having a relatively small lumen, a first end connected to the inflatable member and a second end; an extender having a relatively large lumen, a first end connected to the second end of the catheter and a second end; a working gas for inflating the inflatable member; a pressure source connected to the second end of the extender for supplying the working gas to the extender and for removing the working gas from the extender; and a first valve positioned adjacent the first end of the extender, the first valve having opened and closed conditions, whereby, with the inflatable member in the deflated condition and the first valve in the closed condition, the working gas may be supplied by the pressure source to the extender without placing the inflatable member in the inflated condition, and with the inflatable member in the inflated condition and the first valve in the closed condition, the working gas may be removed by the pressure source from the extender without placing the inflatable member in the deflated condition.

In one embodiment of the apparatus of the present invention, the pressure source may include a chamber having a primary side, a secondary side and a movable member separating the primary side from the secondary side, the secondary side being connected in flow communication with the second end of the extender, a positive pressure source for supplying a positive pressure to the primary side of the chamber to move the movable member toward the secondary side of the chamber, thereby supplying the working gas to the extender, and a negative pressure source for supplying a negative pressure to the primary side of the chamber to move the movable member toward the primary side of the chamber, thereby removing the working gas from the extender to the secondary side of the chamber.

In a preferred embodiment hereof, the medical apparatus may further include a second valve positioned adjacent the second end of the extender, the second valve having opened and closed conditions. In accordance with this embodiment, the pressure source may include a hollow element connected in flow communication with the second end of the extender, whereby, with the second valve in the closed condition, the working gas may be supplied at an inflation pressure to the hollow element without supplying the working gas to the extender, and the working gas may be supplied at a deflation pressure to the hollow element without removing the working gas from the extender. Highly preferred embodiments may further include a variable volume reservoir connected in flow communication with the extender. Preferably, the variable volume reservoir is connected to the extender between the first and second valves.

Yet another aspect of the present invention provides a medical apparatus including an inflatable member having an inflated condition and a deflated condition; a catheter having a relatively small lumen, a first end connected to the inflatable member and a second end; an inflation extender having a relatively large lumen, a first end connected to the second end of the catheter and a second; a deflation extender having a relatively large lumen, a first end connected to the second end of the catheter and a second end; a working gas for inflating the inflatable member; a pressure source connected to the second end of the inflation extender for supplying the working gas to the inflation extender, and connected to the second end of the deflation extender for removing the working gas from the deflation extender; and a first valve positioned adjacent the first end of the inflation extender, the first valve having a first position establishing flow communication between the inflation extender and the catheter, and a closed position interrupting flow communication between the inflation extender and the catheter, whereby, with the inflatable member in the deflated condition and the first valve in the closed position, the working gas may be supplied by the pressure source to the inflation extender without placing the inflatable member in the inflated condition.

In an embodiment of the apparatus in accordance with this aspect of the present invention, the first valve may be positioned adjacent the first end of the deflation extender, the first valve having a second position establishing flow communication between the deflation extender and the catheter and interrupting flow communication between the inflation extender and the catheter, whereby, with the inflatable member in the deflated condition and the first valve in the second position, the working gas may be supplied by the pressure source to the inflation extender without placing the inflatable member in the inflated condition. The first valve in the first position may interrupt flow communication between the deflation extender and the catheter, whereby, with the inflatable member in the inflated condition and the first valve in one of the closed position and the first position, the working gas may be removed by the pressure source from the deflation extender without placing the inflatable member in the deflated condition.

In accordance with preferred embodiments hereof, the apparatus may further include a second valve positioned adjacent the second end of the inflation extender, and the pressure source may include a hollow element connected in flow communication with the second end of the inflation extender, the second valve having a first position establishing flow communication between the hollow element and the inflation extender, and a closed position interrupting flow communication between the hollow element and the inflation extender, whereby, with the second valve in the closed position, the working gas may be supplied to the hollow element without supplying the working gas to the inflation extender, and with the second valve in the first position, the working gas may be supplied from the hollow element to the inflation extender. Highly preferred embodiments may further include a variable volume inflation reservoir connected in flow communication with the inflation extender. The variable volume inflation reservoir may be connected to the inflation extender between the first and second valves.

In more preferred embodiments hereof, the second valve may be positioned adjacent the second end of the deflation extender, the second valve having a second position establishing flow communication between the hollow element and the deflation extender and interrupting flow communication between the hollow element and the inflation extender, whereby, with the second valve in the second position, the working gas may be supplied to the hollow element without supplying the working gas to the inflation extender. The second valve in the first position may interrupt flow communication between the hollow element and the deflation extender, whereby, with the second valve in one of the closed position and the first position, the working gas may be removed from the hollow element without removing the working gas from the deflation extender. Such embodiments may further include a variable volume deflation reservoir connected in flow communication with the deflation extender, preferably between the first and second valves.

In other preferred embodiments hereof, rather than having a first valve positioned adjacent the first end of both the inflation and deflation extenders, the medical apparatus may include a first valve positioned adjacent the first end of the inflation extender and a third valve positioned adjacent the first end of the deflation extender, the third valve having a first position establishing flow communication between the deflation extender and the catheter, and a closed position interrupting flow communication between the deflation extender and the catheter, whereby, with the inflatable member in the inflated condition and the third valve in the closed position, the working gas may be removed by the pressure source from the deflation extender without placing the inflatable member in the deflated condition, and with the inflatable member in the inflated condition and the third valve in the first position, the working gas may be removed from the inflatable member through the catheter to the deflation extender to place the inflatable member in the deflated condition. In such embodiments, rather than having a second valve positioned adjacent the second end of both the inflation and deflation extenders, the apparatus may include a second valve positioned adjacent the second end of the inflation extender and a fourth valve positioned adjacent the second end of the deflation extender, the fourth valve having a first position establishing flow communication between the hollow element and the deflation extender, and a closed position interrupting flow communication between the hollow element and the deflation extender, whereby, with the fourth valve in the closed position, the working gas may be removed from the hollow element without removing the working gas from the deflation extender, and with the fourth valve in the first position, the working gas may be removed from the deflation extender to the hollow element. Such embodiments may further include a variable volume deflation reservoir connected in flow communication with the deflation extender. Desirably, the variable volume deflation reservoir is connected to the deflation extender between the third and fourth valves.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION OF THE PREFERRED EMBODIMENTS

Figure 3:
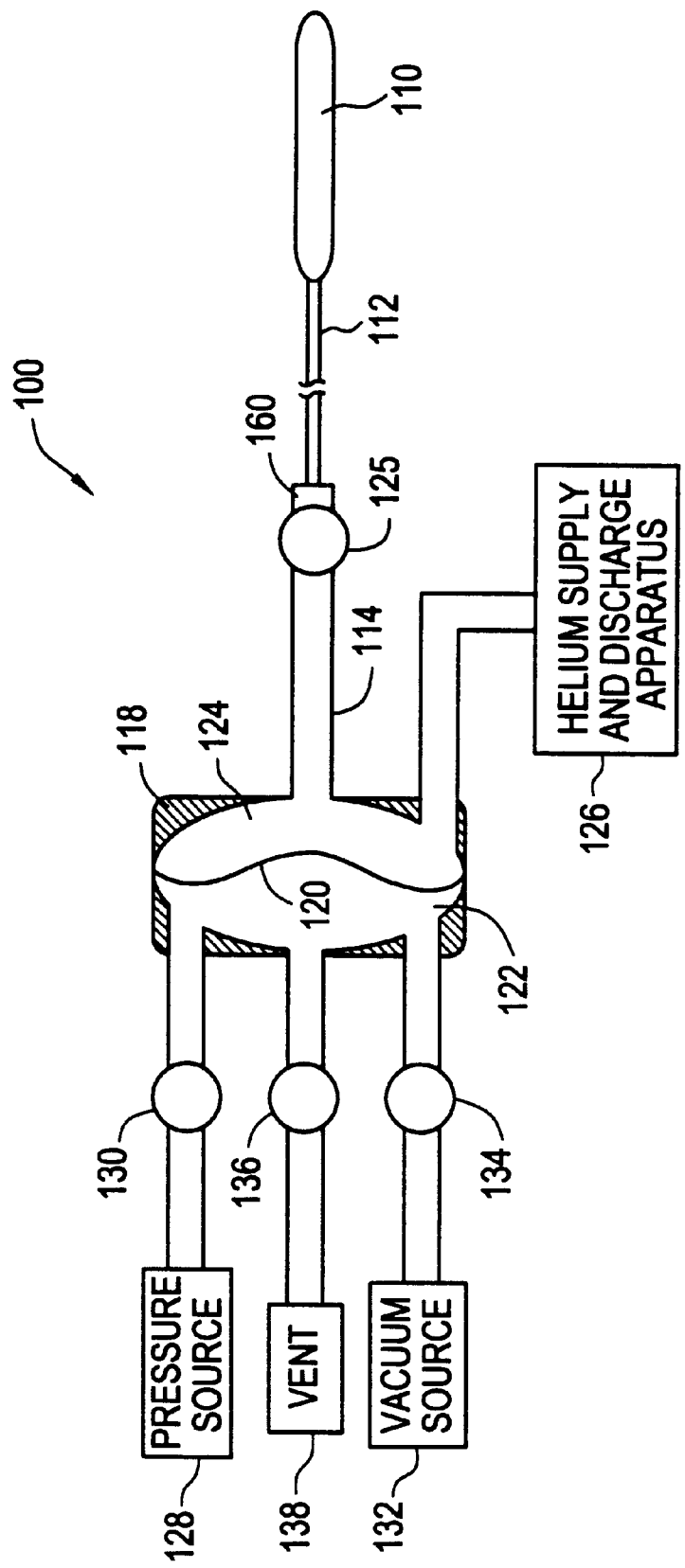
FIG. 3 is a highly schematic view showing a system for inflating and deflating an intra-aortic balloon in accordance with a first embodiment of the present invention.

One embodiment of an intra-aortic balloon pump 100 in accordance with the present invention is shown schematically in FIG. 3. A major portion of balloon pump 100 is similar to the conventional balloon pump 10 described above. Thus, balloon pump 100 includes an isolator 118 divided into a primary side 122 and a secondary side 124 by a pliant membrane 120. Connected to the primary side 122 of isolator 118 are a positive pressure source 128, such as an air compressor or other air supply, a negative pressure source 132, such as a vacuum pump or other vacuum source, and a vent port 138. A solenoid valve 130 controls the flow of air from the positive pressure source toward the isolator, a solenoid valve 134 controls the flow of air from the isolator toward the vacuum source, and a solenoid valve 136 controls the flow of air between the isolator and vent port 138. A controller (not show) controls the operation of solenoid valves 130, 134 and 136 between the open and closed conditions.

On the opposite side of isolator 118, an extender 114 and catheter 112 are connected in series with one another and with an intra-aortic balloon 110 so as to provide flow communication between balloon 110 and the secondary side 124 of isolator 118. A gas source, such as helium supply and discharge apparatus 126, is connected to the secondary side 124 of main isolator 118 to establish and maintain a predetermined volume of helium in the space between membrane 120 and balloon 110. As with the prior art system, extender 114 has a substantially larger diameter than catheter 112, such that the gas flows substantially unrestricted through extender 114, but is constricted in its flow through catheter 112.

Figure 1:
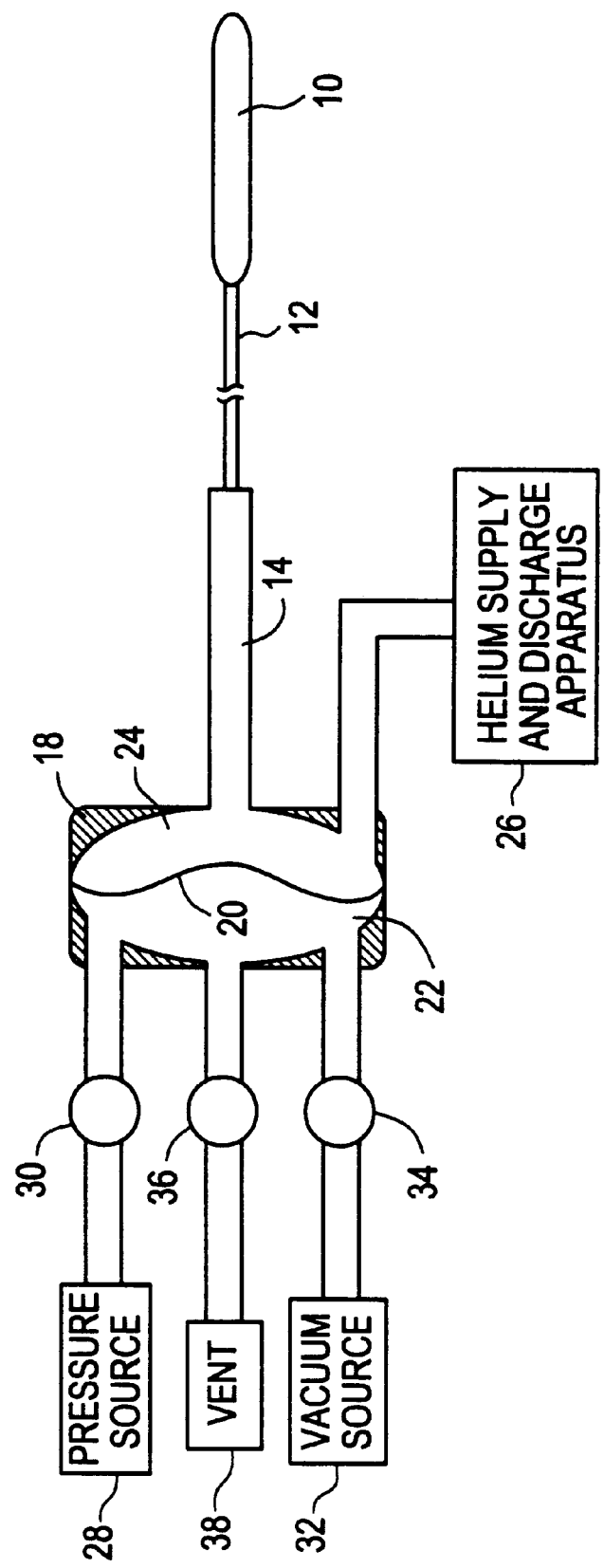
FIG. 1 is a highly schematic view showing a system for inflating and deflating an intra-aortic balloon in accordance with the prior art.
Figure 2:
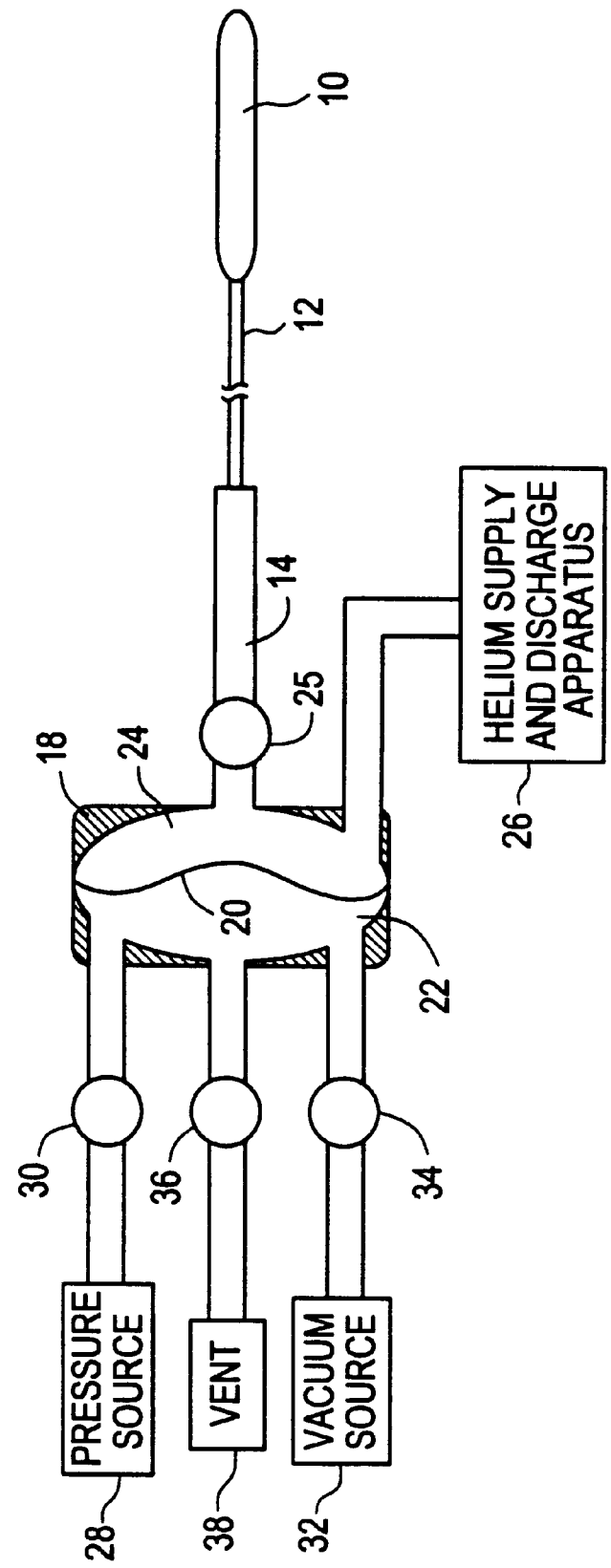
FIG. 2 is a highly schematic view showing an alternate system for inflating and deflating an intra-aortic balloon in accordance with the prior art.

Balloon pump 100 also includes a 2-way solenoid valve 125 between secondary side 124 of isolator 118 and balloon 110. However, rather than being positioned at the end of extender 114 adjacent isolator 118 as in the prior art system illustrated in FIG. 2 and discussed above, valve 125 is positioned as close as possible to the patient. Preferably, valve 125 is positioned at the extreme end of extender 114 adjacent its connection to catheter 112, or in close proximity to the end of extender 114 such that only a short length of extender 160 is extant between valve 125 and catheter 112. As with the other valves in the system, the controller controls the operation of solenoid valve 125 between open and closed conditions.

The following describes the operation of balloon pump 100 to inflate and deflate intra-aortic balloon 110. Assume that the sequence starts with balloon 110 in a fully deflated condition with extender 114 and balloon 110 at an end deflation pressure of about −2 psi; membrane 120 against the wall on primary side 122 of isolator 118; solenoid valves 125, 130 and 136 in a closed state; and solenoid valve 134 open. In a pre-inflation phase, the controller may initially actuate valve 134 to close and valve 136 to briefly open so as to vent the negative pressure from the primary side 122 of isolator 118. The brief opening of valve 136 will cause air at atmospheric pressure to enter primary side 122 through vent port 138 and initiate movement of membrane 120 toward the secondary side 124 of the isolator. Valve 136 may then be closed and valve 130 opened, whereupon air pressure at about 6–8 psi from positive pressure source 128 will pressurize the primary side 122 of isolator 118, moving membrane 120 further toward the secondary side 124. The movement of membrane 120 will force the helium within secondary side 124 toward and into extender 114, producing a pressure in the extender which is about the same as the pressure provided by positive pressure source 128. Since valve 125 is in a closed position during this pre-inflation phase, no helium will flow into catheter 112, and balloon 110 will remain in a deflated condition. In a typical scenario, the buildup of pressure in the extender and in the secondary side of the isolator will cause membrane 120 to reach a state of equilibrium at a spaced distance from its fully extended position against the wall on the secondary side of the isolator (although this is not necessarily the case, and membrane 120 may reach its fully extended position during the pre-inflation phase). Initiating the pre-inflation phase with a venting step is optional since the volume on the primary side 122 of the isolator is small. Where this venting step is not performed, the pre-inflation phase may begin with the controller actuating valve 134 to close and valve 130 to open so as to pressurize the primary side 122 of isolator 118 as described above.

When inflation of balloon 110 is desired, the controller may actuate valve 125 to open. Since balloon 110 is at a negative pressure and extender 114 is at a positive pressure, helium will begin to flow through catheter 112 to the balloon. Balloon 110 thus will begin to inflate, producing an immediate pressure within the balloon approximately equal to the blood pressure of the patient, e.g., about 2 psi. As helium flows through catheter 112 to inflate balloon 110, membrane 120 may continue to move forward to replace the helium leaving extender 114 with helium from the secondary side 124 of isolator 118, thus maintaining the pressure in the extender at a substantially constant level during at least the initial portion of the inflation cycle. Depending upon the volume relationship between isolator 118 and extender 114, membrane 120 may contact the wall on the secondary side 124 of the isolator before balloon 110 has been fully inflated. In such event, balloon 110 will continue to inflate as the pressure in extender 114 begins to decay until balloon 110 reaches the fully inflated condition. Since, at the initiation of the inflation phase, valves 130, 134 and 136 are already in the proper state for inflation, membrane 120 is already displaced toward the secondary side 124 of isolator 118, and secondary side 124 and, in particular, extender 114 are already fully pressurized, inflation of balloon 110 is able to proceed more rapidly than with the systems of the prior art, including the system shown in FIG. 2.

When balloon 110 has reached a desired state of inflation, the controller may operate to close valves 125 and 130. The closure of valve 130 will terminate the application of positive pressure to isolator 118, and the closure of valve 125 will prevent the flow of helium in either direction through catheter 112 between extender 114 and balloon 110, thereby ensuring that no deflation or further inflation of the balloon occurs. Subsequently, or at the same time, the controller may initiate a pre-deflation phase by briefly opening valve 136 to release the positive pressure from primary side 122 of isolator 118 to the atmosphere through vent port 138. As this venting step takes place, membrane 120 may begin moving toward the primary side 122 of isolator 118, drawing helium out of extender 114 so as to decrease the pressure therein. However, since valve 125 remains closed, no deflation of balloon 110 will take place. This venting step will reduce the amount of air which negative pressure source 132 must remove from primary side 122 during deflation, and thus will reduce the overall power consumed by intra-aortic balloon pump 100 during the deflation cycle. After a short time interval, valve 136 may be closed and valve 134 opened so that negative pressure at about −3 to −7 psi from vacuum source 132 evacuates the primary side 122 of isolator 118, drawing membrane 120 further toward, but typically not against, the wall on primary side 122. This movement of membrane 120 will draw a further volume of helium out from extender 114 and into the secondary side 124 of the isolator, reducing the pressure in the extender significantly, and, more particularly, to about the same negative pressure as provided by vacuum source 132.

When deflation of balloon 110 is desired, valve 125 may be opened and, as a result of the pressure differential across catheter 112, helium will flow out from balloon 110 through catheter 112 to extender 114. As helium flows from balloon 110 into extender 114, membrane 120 may continue to move toward the wall on primary side 122, drawing into the secondary side 124 of the isolator a volume of helium equal to that entering the extender from the balloon, and thus maintaining a substantially constant negative pressure in the extender throughout a significant portion of the deflation cycle. Again, depending upon the relationship between the volume of the isolator and the volume of the extender, membrane 120 may contact the wall on the primary side 122 of the isolator before balloon 110 has been fully deflated. In such case, the pressure in extender 114 will begin to increase as the deflation of balloon 110 continues, causing the rate of deflation to decay over the remainder of the deflation cycle until the fully deflated condition of balloon 110 is achieved. Since, when the deflation cycle is begun, valves 130, 134 and 136 are already in the proper state for deflation, membrane 120 is already displaced toward the primary side 122 of isolator 118, and secondary side 124 and, in particular, extender 114, are already at about the same negative pressure as vacuum source 132, deflation of balloon 110 will proceed more rapidly than with prior art systems. When balloon 110 has been fully deflated, the controller may operate to close valve 125, preventing helium from flowing in either direction through catheter 112 between extender 114 and balloon 110, thereby completing one inflation/deflation cycle and placing intra-aortic balloon pump 100 in condition to initiate a next pre-inflation phase.

Positioning valve 125 at or near the end of extender 114 adjacent catheter 112 provides several advantages in addition to faster response times. Firstly, since a lower volume of helium has to pass through the valve during the inflation and deflation cycles, the size of the valve may be reduced from that required in the system of FIG. 2. This reduction in size may allow for faster mechanical switching of the valve between open and closed conditions, resulting in still further improvements in inflation and deflation cycle times. Moreover, since valve 125 may be a simple electrically operated in-line valve, the valve may be made inexpensively so as to be disposable along with extender 114, catheter 112 and balloon 110. In addition, once an electrical wire is positioned along the extender to transmit electrical signals to the valve, it is a simple matter to place a sensor, such as a pressure transducer or blood leak detector, in the vicinity of the valve, resulting in more accurate measurements, faster leak detection, more reliable information as to locations of any kinks, etc.

In a variant of the system described above, intra-aortic balloon pump 100 may incorporate an overdrive system, such as the oversized isolator or secondary isolator or isolators described in U.S. Pat. No. 5,817,001, the disclosure of which is hereby incorporated by reference herein. Such systems maintain a substantially constant inflation or deflation pressure in the extender for a longer period of time so as to inflate and deflate the balloon more rapidly. In one such system, the isolator may be designed to have a volume which is larger than that of a conventional isolator. During the pre-inflation phase in such system, opening valve 130 will cause membrane 120 to move toward the secondary side 124 of the isolator as pressurized air from pressure source 128 flows into the primary side 122 thereof. However, equilibrium will be reached and membrane 120 will come to rest with a greater volume of gas available in the secondary side 124 of the isolator than in the system described immediately above. As a result, membrane 120 will continue to move toward the wall on the secondary side of the isolator, and the pressure in extender 114 will be maintained at a substantially constant level, throughout the entire or substantially the entire inflation phase, thereby minimizing or eliminating any increase in cycle time resulting from pressure decay in the extender during inflation. Providing the isolator with an appropriate volume will enable the inflation cycle to be terminated by closing valve 125 just as membrane 120 contacts the wall on the secondary side 124 of the isolator.

The deflation process using an intra-aortic balloon pump 100 incorporating an overdrive system may operate in a similar fashion. That is, during the pre-deflation phase, opening valve 134 will cause membrane 120 to begin moving toward the primary side 122 of the isolator as vacuum source 132 draws air out therefrom. When membrane 120 comes to rest at a state of equilibrium, a greater volume will be extant on the primary side of the isolator than with the system described above. Accordingly, membrane 120 will continue to move toward the wall on primary side 122, and the pressure in extender 114 will remain at a substantially constant level, throughout all or substantially all of the deflation phase, minimizing or eliminating any increase in cycle time resulting from a gradual pressure increase in the extender during deflation. When the isolator is provided with an appropriate volume, the deflation cycle may be terminated by closing valve 125 just as membrane 120 contacts the wall on the primary side 122 of the isolator.

Figure 4:
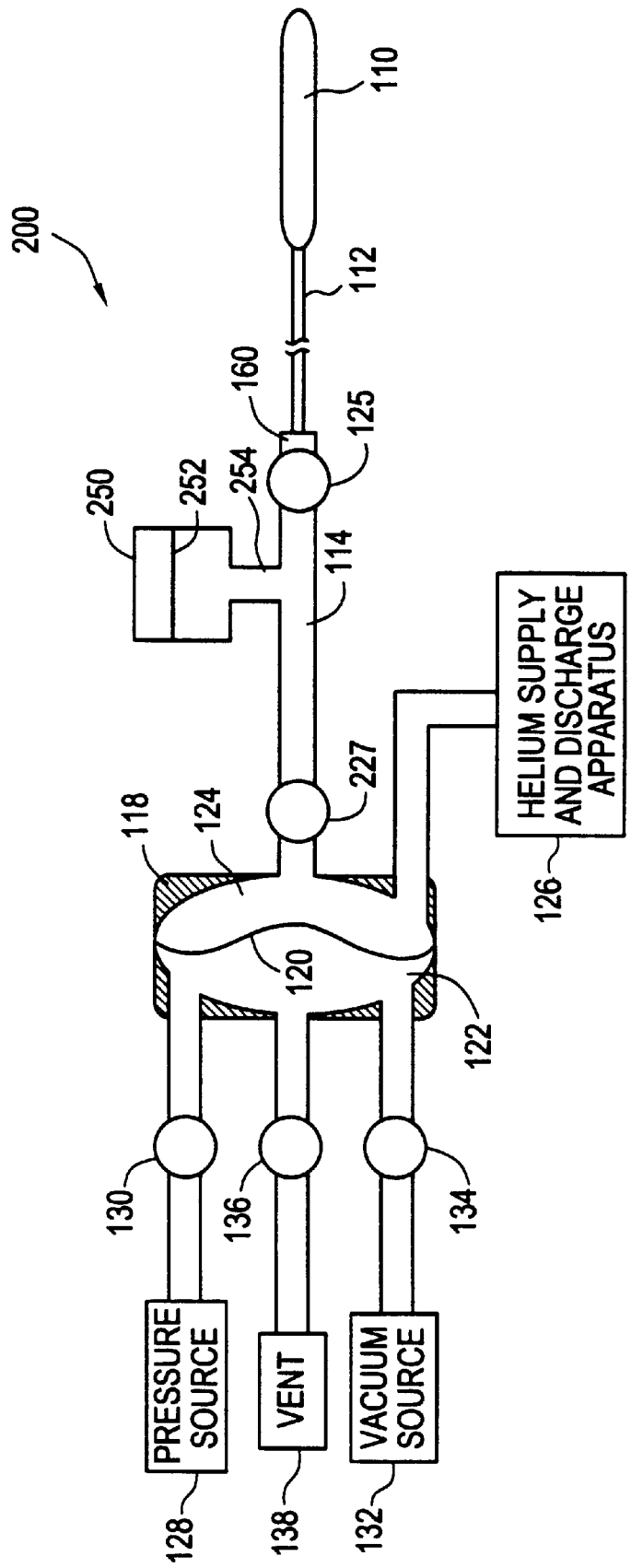
FIG. 4 is a highly schematic view showing a system for inflating and deflating an intra-aortic balloon in accordance with a second embodiment of the present invention.

FIG. 4 illustrates an intra-aortic balloon pump 200 in accordance with a further variant of the system described above. In accordance with this variant, intra-aortic balloon pump 200 includes an accumulator 250 connected to extender 114 between isolator 118 and valve 125 through an inlet/outlet port 254. In addition to accumulator 250, intra-aortic balloon pump 200 includes a second 2-way solenoid valve 227 between the secondary side 124 of isolator 118 and extender 114.

Accumulator 250 consists of a housing having a predetermined maximum volume, with a piston or membrane 252 slidably assembled therein so as to vary the volume in flow communication with port 254. Accumulator 250 may be a mechanical accumulator in which piston or membrane 252 is biased toward a neutral position near the center of the accumulator by a spring (not shown). As piston or membrane 252 is moved forward or backward away from the neutral position, the spring will act to push or pull it back toward the neutral position.

Preferably, accumulator 250 is a gas accumulator in which piston or membrane 252 is biased toward the neutral position by a trapped gas, and would thus react more quickly to pressure changes than mechanical accumulators. In a gas accumulator, increasing the pressure acting on piston or membrane 252 to a pressure greater than that of the trapped gas will cause the piston or membrane to move backward away from port 254, compressing the trapped gas and increasing its pressure until equilibrium is reached. When the applied pressure is reduced, the trapped gas will expand and push the piston or membrane back toward the neutral position. Conversely, decreasing the pressure acting on the piston or membrane to a pressure lower than that of the trapped gas will cause the piston or membrane to move forward toward port 254, reducing the pressure of the trapped gas until equilibrium is reached. When the applied pressure is then increased, the trapped gas will be compressed, drawing the piston or membrane back toward the neutral position. In gas accumulators, if the maximum volume of the accumulator is large relative to the volume of trapped gas, low pressures acting on piston or membrane 252 may displace it forward or backward, depending upon whether the pressure is greater than or less than the pressure of the trapped gas. At these low pressures, the trapped gas will exert more uniform pressure as the piston or membrane is pushed forward, and will compress more uniformly as the piston or membrane is pushed backward.

The operation of intra-aortic balloon pump 200 to inflate balloon 110 may begin with a pre-inflation phase. This phase may begin with balloon 110 in a fully deflated condition, membrane 120 in a fully retracted condition against the wall on primary side 122 of isolator 118, valves 130 and 136 closed and valves 134, 125 and 227 open. Initially, the controller may operate to close valves 134, 125 and 227, and, optionally, to briefly open valve 136 to vent the negative pressure from the primary 122 of the isolator, initiating movement of membrane 120 toward the secondary side 124 thereof. Valve 136 may then be closed and valve 130 opened, causing membrane 120 to move further toward the secondary side 124 of the isolator as positive pressure flows into the primary side 122 thereof. Since valve 227 is closed at this juncture, helium will not flow into extender 114, but rather will build up pressure in the secondary side of the isolator. After a small delay, valve 227 may be opened, causing membrane 120 to move further toward the secondary side 124 of the isolator and forcing the helium within secondary side 124 to flow not only into extender 114, but also into accumulator 250. The flow of helium into accumulator 250 will push piston 252 backward against the force of the biasing spring or gas, depending upon the type of accumulator used, until a state of equilibrium is reached in which the forces acting on the piston from both sides are equal. Because of the added volume of accumulator 250, membrane 120 will typically reach its fully extended position against the wall on the secondary side 124 of the isolator during this pre-inflation phase, at which point valves 130 and 227 may be closed, cutting off isolator 118 from the closed portion of the system. Once valve 227 has been closed, isolator 118 may immediately begin a pre-deflation phase, as described below, even though the inflation of balloon 110 has not yet begun.

Upon opening valve 125 to inflate balloon 110, helium will flow from extender 114 through catheter 112 to the balloon. As helium flows out from extender 114 and from accumulator 250, the forces acting on piston 252 will no longer be equal. As a result, the biasing force exerted on piston 252 will push the piston forward toward its neutral position, reducing the overall volume of the extender/accumulator combination and thus maintaining the pressure therein at a substantially constant level. Preferably, the volume of accumulator 250 is such that movement of piston 252 from the retracted position to or toward the neutral position will displace a sufficient amount of helium to maintain the pressure in the extender at a substantially constant level during the entire inflation cycle. If membrane 120 does not reach its fully extended position against the wall on the secondary side 124 of the isolator during the pre-inflation phase, valves 130 and 227 will typically remain open during inflation until such time as membrane 120 reaches its fully extended position, at which time valves 130 and 227 may be closed. Once balloon 110 has been fully inflated, valve 125 may be closed to isolate the balloon from the remainder of the system.

As noted above, the pre-deflation phase may begin once membrane 120 has reached its fully extended position and valve 227 has been closed. Thus, this step may occur independently of whether or not inflation has taken place. In the pre-deflation phase, the controller may close valve 130 and open valve 136 briefly to vent the positive pressure from the primary side 122 of isolator 118, at which point membrane 120 may begin moving toward the primary side. As valve 136 then is closed and valve 134 is opened, membrane 120 will move further toward the primary side 122 of the isolator, creating a negative pressure on the secondary side 124 thereof. After a brief delay, and with valve 125 in a closed position, valve 227 may be opened, causing membrane 120 to move still further toward the primary side 122 as helium is drawn out from extender 114 and accumulator 250 into the secondary side 124 of the isolator. The flow of helium out from accumulator 250 will pull piston 252 away from the neutral position and toward port 254 against the biasing force until an equilibrium state is reached. Because of the added volume of helium available in accumulator 250, membrane 120 will typically bottom out against the wall on the primary side 122 of the isolator during this pre-deflation phase, at which point valves 134 and 227 may be closed, again cutting off isolator 118 from the closed portion of the system. When valve 227 has been closed following the pre-deflation phase, isolator 118 may begin a next pre-inflation phase, even though balloon 110 has yet to be deflated.

Upon opening valve 125 to deflate balloon 110, helium will flow from balloon 110 through catheter 112 into extender 114. As helium flows into extender 114 and into accumulator 250, piston 252 will no longer be in a state of equilibrium. The pressure differential acting on piston 252 will push the piston rearward toward its neutral position, increasing the overall volume of the extender/accumulator combination and thus maintaining the pressure therein at a substantially constant level. Desirably, accumulator 250 has a volume such that movement of piston 252 from the forward position to or toward the neutral position will displace a sufficient amount of helium to maintain a substantially constant negative pressure in the extender during the entire deflation cycle. Once balloon 110 has reached full deflation, valve 125 may be closed and the process repeated.

As noted, the incorporation of accumulator 250 in intra-aortic balloon pump 200 permits the pre-deflation phase to be performed either during or prior to inflation of balloon 110. As a result, very rapid cycling of balloon 110 between inflated and deflated conditions can be achieved. This capability thus enables intra-aortic balloon pump 200 to be used effectively to assist patients having high heart rates.

In a variant of the system illustrated in FIG. 4, accumulator 250 may be deleted from intra-aortic balloon pump 200 and, in its place, extender 114 may be formed with a larger volume, such as by increasing its length. Where the volume of extender 114 is made sufficiently large, membrane 120 will reach its fully extended position against the wall on the secondary side 124 of isolator 118 either as valve 227 is opened during the pre-inflation phase or after valve 125 has been opened and balloon 110 begins to inflate, but before inflation is fully completed. When membrane 120 reaches its fully extended position, valves 130 and 227 may be closed while valve 125 remains open. The closure of valve 227 will permit the controller to initiate a pre-deflation phase even though the inflation of balloon 110 may not have been completed or, in fact, may not have even started. With membrane 120 in its fully extended position and valve 227 closed, the pressure in extender 114 will begin to decay as the inflation of balloon 110 continues until a desired degree of inflation is achieved. It will be appreciated that this decay (as well as the decay occurring during deflation) may be eliminated by employing an overdrive system as described above.

If the volume of extender 114 is sufficiently large, membrane 120 will reach its fully retracted position against the wall on the primary side 122 of isolator 118 either when valve 227 is opened during the pre-deflation step, or after valve 125 has been opened to begin deflation, but before deflation has been completed. When membrane 120 reaches its fully retracted position, valves 134 and 227 may be closed, while valve 125 remains open. The closure of valve 227 will permit the controller to initiate a pre-inflation phase even though the deflation of balloon 110 may not have been completed or even started. With membrane 120 in its fully retracted position and valve 227 closed, the rate of deflation of balloon 110 will slow as the pressure in extender 114 gradually increases until a desired state of deflation is achieved. As noted above, an overdrive system may be employed to avoid this decay in the deflation rate.

Despite the improvements in response time they provide, the pneumatic efficiency of intra-aortic balloon pumps 100 and 200, as with the balloon pump systems of the prior art, is hampered by the need to pressurize and depressurize extender 114 during every inflation/deflation cycle. In the embodiments of the invention described below, this pneumatic inefficiency is reduced or eliminated by replacing the single extender 114 with separate pressure and vacuum extenders.

Figure 5:
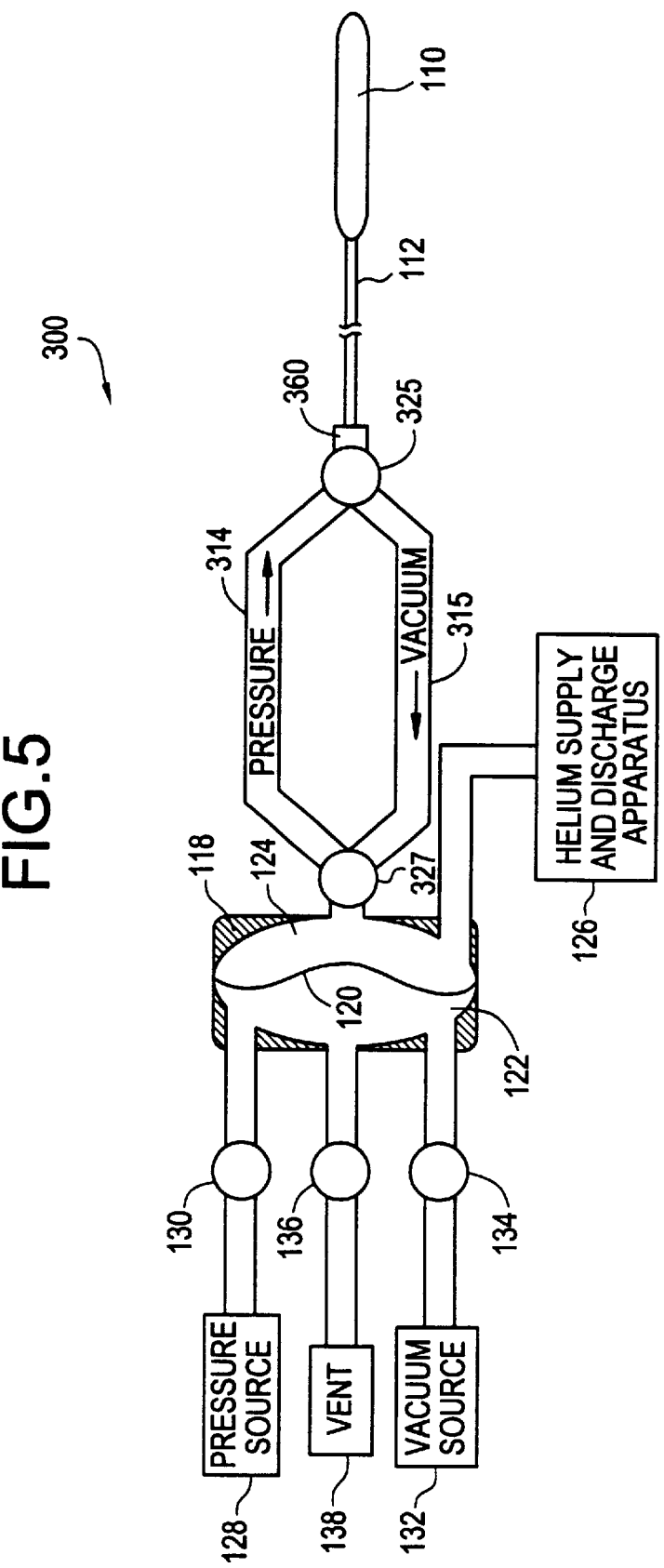
FIG. 5 is a highly schematic view showing a system for inflating and deflating an intra-aortic balloon in accordance with a third embodiment of the present invention.

One embodiment of an intra-aortic balloon pump 300 in accordance with this variant is shown schematically in FIG. 5. Balloon pump 300 is similar to balloon pump 100 described above. However, rather than a single extender 114 between isolator 118 and catheter 112, balloon pump 300 includes a first extender 314 for supplying positive pressure to balloon 110, and a second extender 315 connected in parallel to extender 314 for supplying negative pressure or vacuum to balloon 110. At their ends adjacent catheter 112, extenders 314 and 315 may be connected to a solenoid valve 325. Valve 325 is preferably a three-way valve having a first position open to extender 314 and closed to extender 315, a second position closed to extender 314 and open to extender 315, and a third position closed to both extenders 314 and 315. Valve 325 may be connected directly to catheter 112, or a short length of extender 360 may be interposed between valve 325 and catheter 112. At their ends adjacent isolator 118, extenders 314 and 315 may be connected to a solenoid valve 327 which may be a three-way valve similar to valve 325.

As with intra-aortic balloon pump 100, the inflation of balloon 110 using intra-aortic balloon pump 300 begins with a pre-inflation step. Starting with balloon 110 in a fully deflated condition, membrane 120 will be in a fully retracted condition, valves 130 and 136 will be closed, valve 134 will be open, and valves 325 and 327 will be open to flow through extender 315. The controller initially may actuate valves 134, 325 and 327 to fully closed positions, isolating extender 315 and the vacuum conditions extant therein. Subsequently, or at the same time, valve 136 optionally may be opened momentarily so as to vent the negative pressure from the primary side 122 of isolator 118, initiating movement of membrane 120 toward the secondary side 124 thereof. After valve 136 is closed, valve 130 may be opened, causing membrane 120 to move further toward secondary side 124. However, since valve 327 is closed, helium will not flow into extenders 314 or 315, but rather will build up pressure in the secondary side of the isolator. After a small delay, valve 327 may be opened to flow communication with extender 314, causing membrane 120 to move still further toward secondary side 124 and helium to flow into extender 314 until a state of equilibrium is reached, typically with membrane 120 at a spaced distance from the wall on the secondary side of the isolator, and the pressure in both the extender 314 and in the secondary side 124 of the isolator about equal to the pressure in the primary side 122 of the isolator. Since there is already helium at a positive pressure in extender 314 from the previous inflation cycle (as will be appreciated from the description hereinbelow), less helium will move from the secondary side 124 of the isolator into the extender 314 in order to reach a state of equilibrium.

With valve 325 in a closed position during this pre-inflation phase, no helium will flow into catheter 112, and no inflation of balloon 110 will take place. However, since extender 314 is already in a substantially pressurized condition before the pre-inflation phase takes place, less movement of helium gas is needed and intra-aortic balloon pump 300 will inflate balloon 110 with a greater pneumatic efficiency than does intra-aortic balloon pump 100.

To start inflation, valve 325 is opened to flow communication with extender 314 so that helium will begin to flow through catheter 112 to balloon 110. As balloon 110 inflates, membrane 120 will move forward to replace the helium leaving extender 314 with helium from the secondary side 124 of the isolator, thus maintaining the pressure in the extender at a substantially constant level for at least a significant portion of the inflation cycle. Depending upon the volume relationship between extender 314 and isolator 118, membrane 120 may or may not reach its fully extended position against the wall on the secondary side 124 of isolator 118 during the inflation step. Where membrane 120 does not reach its fully extended position before balloon 110 has been inflated to the desired volume, inflation may be terminated by closing valve 325. Valves 130 and 327 may also be closed, trapping helium at a positive pressure within extender 314. At the same time or immediately thereafter, the controller may initiate a pre-deflation phase by briefly opening valve 136 to vent the primary side 122 of isolator 118, initiating movement of membrane 120 toward the primary side of the isolator. Since valve 327 remains closed, no helium will be drawn out from extender 314, which thus remains in a positive pressure state, or from extender 315, which remains in a negative pressure state. As valve 136 is closed, valve 134 may be opened to begin evacuating the primary side 122 of the isolator. After a momentary delay, valve 327 may be opened to flow communication with extender 315, causing membrane 120 to move further toward the primary side 122 until equilibrium is reached with membrane 120 at a spaced distance from the wall on the primary side of the isolator. At this juncture, the pressure in both the extender 315 and in the secondary side 124 of the isolator will be at about the same negative pressure as the primary side 122 of the isolator. Since helium at a negative pressure already exists in extender 315 from the previous deflation cycle, less helium will need to be removed from extender 315 in order to reach this equilibrium state, resulting in greater pneumatic efficiency. The fact that valve 325 remains in a closed position during this pre-deflation phase will prevent balloon 110 from deflating.

When balloon 110 is to be deflated, valve 325 may be opened to flow communication with extender 315 so that helium will begin to flow out from balloon 110 through catheter 112 to extender 315. As balloon 110 deflates, membrane 120 will move toward the wall on primary side 122, drawing helium out from extender 315 into the second side 124 of the isolator, thereby maintaining a substantially constant negative pressure in the extender throughout at least a significant portion of the deflation cycle. Again, depending upon the volume relationship between isolator 118 and extender 315, membrane 120 may or may not reach its fully retracted position against the wall on the primary side 122 of isolator 118 during deflation. Where membrane 120 does not reach its fully retracted position before balloon 110 has achieved a desired degree of deflation, deflation may be terminated by closing valve 325. Valves 134 and 327 may also be closed, trapping helium at a negative pressure within extender 315 and placing intra-aortic balloon pump 300 in condition for a next pre-inflation cycle.

The use of separate inflation and deflation extenders provides a further advantage in addition to greater pneumatic efficiency. More particularly, if the system detects an arrhythmia (i.e., the onset of a premature heart beat), the controller may immediately terminate inflation and initiate deflation simply by switching valve 325 from flow communication with extender 314 to flow communication with extender 315. The existence of a negative pressure in extender 315 will permit deflation of balloon 110 to begin immediately. Although this procedure may cause the next inflation cycle to be missed, the importance of this capability will be readily appreciated to those of ordinary skill in the art.

As noted above, depending upon the volume relationship between isolator 118 and extenders 314 and 315, membrane 120 may or may not reach its fully extended position during inflation of balloon 110 or its fully retracted position during deflation of balloon 110. In a variant of the foregoing system, intra-aortic balloon pump 300 may be modified to ensure that membrane 120 reaches its fully extended position during inflation and its fully retracted position during deflation by increasing the volume of extenders 314 and 315, such as by increasing their lengths, without increasing the volume of isolator 118. As will be explained below, ensuring that membrane 120 reaches its fully extended position before balloon 110 has been fully inflated and its fully retracted position before balloon 110 has been fully deflated will enable more rapid cycling of balloon 110 between inflated and deflated conditions.

Thus, where the volume of extender 314 is sufficiently large, membrane 120 will reach its fully extended position against the wall on the secondary side 124 of isolator 118 either as valve 327 is opened during the pre-inflation step or after valve 325 has been opened to flow communication with extender 314 and balloon 110 begins to inflate, but before inflation has been completed. When membrane 120 reaches its fully extended position, valves 130 and 327 may be closed while valve 325 remains open. The closure of valve 327 will permit the controller to initiate a pre-deflation phase even though the inflation of balloon 110 may not have been completed or even started. With membrane 120 in its fully extended position and valve 327 closed, the pressure in extender 314 will begin to decay as the inflation of balloon 110 continues until a desired degree of inflation is achieved. It will be appreciated that the overdrive systems described above may be used to eliminate the pressure decay during inflation (as well as during deflation), enabling inflation to be achieved more rapidly.

During the deflation portion of the cycle, if the volume of extender 315 is sufficiently large, membrane 120 will reach its fully retracted position against the wall on the primary side 122 of the isolator either when valve 327 is opened during the pre-deflation step, or after valve 325 has been opened to flow communication with extender 315 to begin deflation, but before deflation has been completed. When membrane 120 reaches its fully retracted position, valves 134 and 327 may be closed, while valve 325 remains open. The closure of valve 327 will isolate isolator 118 from the extenders, thereby enabling the controller to initiate a pre-inflation step even though the deflation of balloon 110 may not have been started or completed. With membrane 120 in its fully retracted position and valve 327 closed, the rate of deflation of balloon 110 will gradually decrease as the pressure in extender 315 gradually increases until a desired state of deflation is achieved. Again, an overdrive system may be employed to avoid the gradual decrease in the deflation rate.

In the discussion above, it was noted that, with the configuration of intra-aortic balloon pump 300, extender 314 always includes helium at a substantial positive pressure therein, and extender 315 always includes helium at a substantial negative pressure therein. Thus, increasing the length of extender 314 has the effect of creating a larger reservoir of helium at a positive pressure, and increasing the length of extender 315 has the effect of creating a larger reservoir of helium at a negative pressure. As valve 327 is opened to either positive pressure or negative pressure, depending on the point in the inflation/deflation cycle, very little change takes place in the pressure within each extender. Rather, whatever helium is forced into extender 314 from the isolator is approximately equal to the amount of helium which is pushed out the other end of the extender into the balloon. Similarly, the amount of helium which is drawn out from the extender by the isolator is approximately equal to the amount of helium which enters the extender from the balloon. Since there is little, if any, change in the pressure in the extenders during each inflation/deflation cycle and since the volumes of the extenders have little or no affect on the inflation and deflation of the balloon, the extenders can be made as long as desired. Increasing the length of the extenders allows several advantages to be realized, one of which is the ability to increase the amount of movement which may take place between the intra-aortic balloon pump and the patient so that transporting the patient from one location to another is made easier. Furthermore, moving the intra-aortic balloon pump farther from the patient will permit greater access to the patient during emergency situations, and will reduce the impact of the noise emanating from the balloon pump on the patient.

Figure 6:
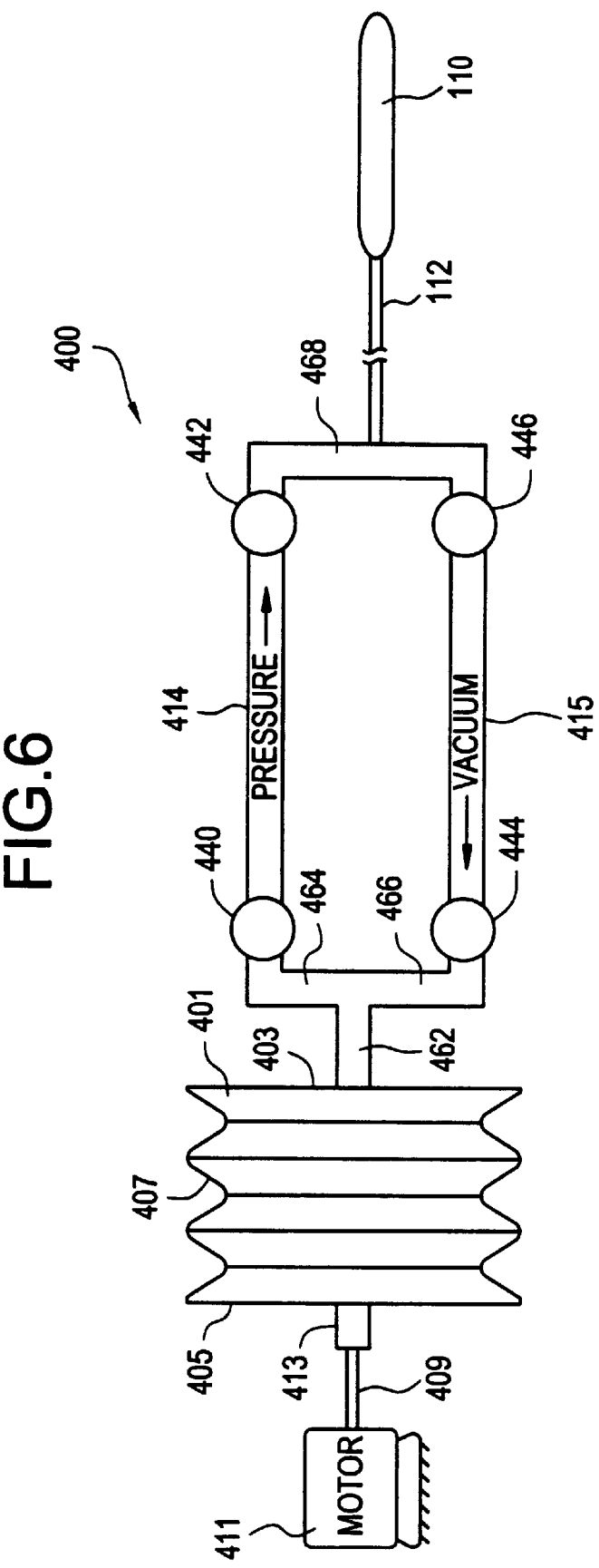
FIG. 6 is a highly schematic view showing a system for inflating and deflating an intra-aortic balloon in accordance with a fourth embodiment of the present invention.

The principles of the present invention may be used in connection with intra-aortic balloon pumps which utilize an arrangement other than an isolator for the controlled inflation and deflation of the balloon. One such system, sold by Arrow International Investment Corp. of Everett, Massachusetts under the trademark KAAT II PLUS, utilizes a bellows to effect inflation and deflation. One embodiment of an intra-aortic balloon pump 400 incorporating a bellows system is shown schematically in FIG. 6, although it should be appreciated that a bellows system may be used in place of an isolator in all of the intra-balloon pump embodiments described herein. Balloon pump 400 differs from balloon pump 300 described above principally in two respects. Firstly, in place of isolator 118, balloon pump 400 includes a bellows 401 having a rigid stationary front plate 403, a rigid movable back plate 405 and an expandable and collapsible side wall 407. The shaft 409 of a stepper motor 411 is threadedly connected to back plate 405 through a lead screw 413 so that rotation of stepper motor 411 in a forward or reverse direction results in a corresponding forward or backward linear movement of bellows back plate 405.

Intra-aortic balloon pump 400 also differs from balloon pump 300 in that, rather than using 3-way valves 325 and 327, intra-aortic balloon pump 400 includes separate two-way valves at each end of pressure extender 414 and at each end of vacuum extender 415. Thus, extender 414 may include one solenoid valve 440 at its end closest to bellows 401, and another solenoid valve 442 at its end closest to catheter 112. Similarly, extender 415 may include one solenoid valve 444 at its end closest to bellows 401, and another solenoid valve 446 at its end closest to catheter 112. Valves 440 and 444 may be connected to the output of bellows 401 by an extender portion 462 having branches 464 and 466 leading to the respective valves. Similarly, valves 442 and 446 may be connected to catheter 112 by a common extender portion 468.

As with the other embodiments hereof, the first step in inflating balloon 110 using intra-aortic balloon pump 400 may be a pre-inflation step. As this step begins, balloon 110 will be in a fully deflated condition, bellows 401 will have an expanded volume, valves 440 and 442 will be closed, and valves 444 and 446 will be open so that there is flow through extender 415. The controller may initially actuate valves 444 and 446 to close, isolating extender 415 under vacuum conditions. Subsequently, the controller may actuate stepper motor 411 to rotate shaft 409 a predetermined number of revolutions in, for example, a clockwise direction so as to push bellows back plate 405 forward. This motion has the affect of reducing the internal volume of bellows 401 by a predetermined amount. Since valves 440 and 444 are closed, helium will not flow into extender 414 or 415, but rather will build up pressure within bellows 401. After a small delay, valve 440 may be opened, causing helium to flow into extender 414. Because extender 414 already included helium at a positive pressure from the previous inflation cycle (as will be appreciated from the description hereinbelow), little helium will move from bellows 401 into extender 414 during this pre-inflation phase. With valve 442 remaining in a closed position, no helium will flow from extender 414 into balloon 110. To effect inflation, valve 442 may be opened, enabling helium to flow through common extender portion 468 and catheter 112 to balloon 110. Helium will not flow into extender 415 because valve 446 is closed. The fact that extender 414 is at least partially pressurized before the pre-inflation phase commences increases the pneumatic efficiency of intra-aortic balloon pump 400.

After inflation of balloon 110 has been completed, valves 440 and 442 may be closed, trapping helium at a positive pressure within extender 414. At the same time or immediately thereafter, the controller may initiate a pre-deflation phase. Unlike intra-aortic balloon pumps using an isolator 118, there is no air in bellows 401, and therefore no need to initiate the pre-deflation phase with a venting step. Rather, to begin the pre-deflation phase, stepper motor 411 may be actuated to rotate shaft 409 a predetermined number of revolutions in a counterclockwise direction so as to pull bellows back plate 405 rearward. This motion has the effect of increasing the internal volume of bellows 401 by a predetermined amount so as to create a negative pressure therein. The fact that valves 440 and 444 are closed prevents helium from flowing from extender 414 or 415 into bellows 401. After a small delay, valve 444 may be opened, causing helium to flow from extender 415 into bellows 401. However, since extender 415 is already at a negative pressure when valve 444 is opened, little helium will move from extender 415 into the bellows during this pre-deflation phase. No deflation of balloon 110 will occur at this stage since valve 446 is still closed. To effect deflation, valve 446 may be opened, enabling helium to flow from balloon 110 through catheter 112 and common extender portion 468 to extender 415. No helium will flow into extender 414 because valve 442 is closed. The fact that extender 415 is already at a negative pressure before the pre-deflation phase commences contributes to the overall increased pneumatic efficiency of intra-aortic balloon pump 400. It will be appreciated that, as with intra-aortic balloon pump 300 described above, extenders 414 and 415 may be formed with large volumes relative to the volume of bellows 401 so that the pre-deflation phase may be initiated before the inflation of balloon 110 has been completed, and so that the pre-inflation phase may be initiated before balloon 110 has been fully deflated.

Figure 7:
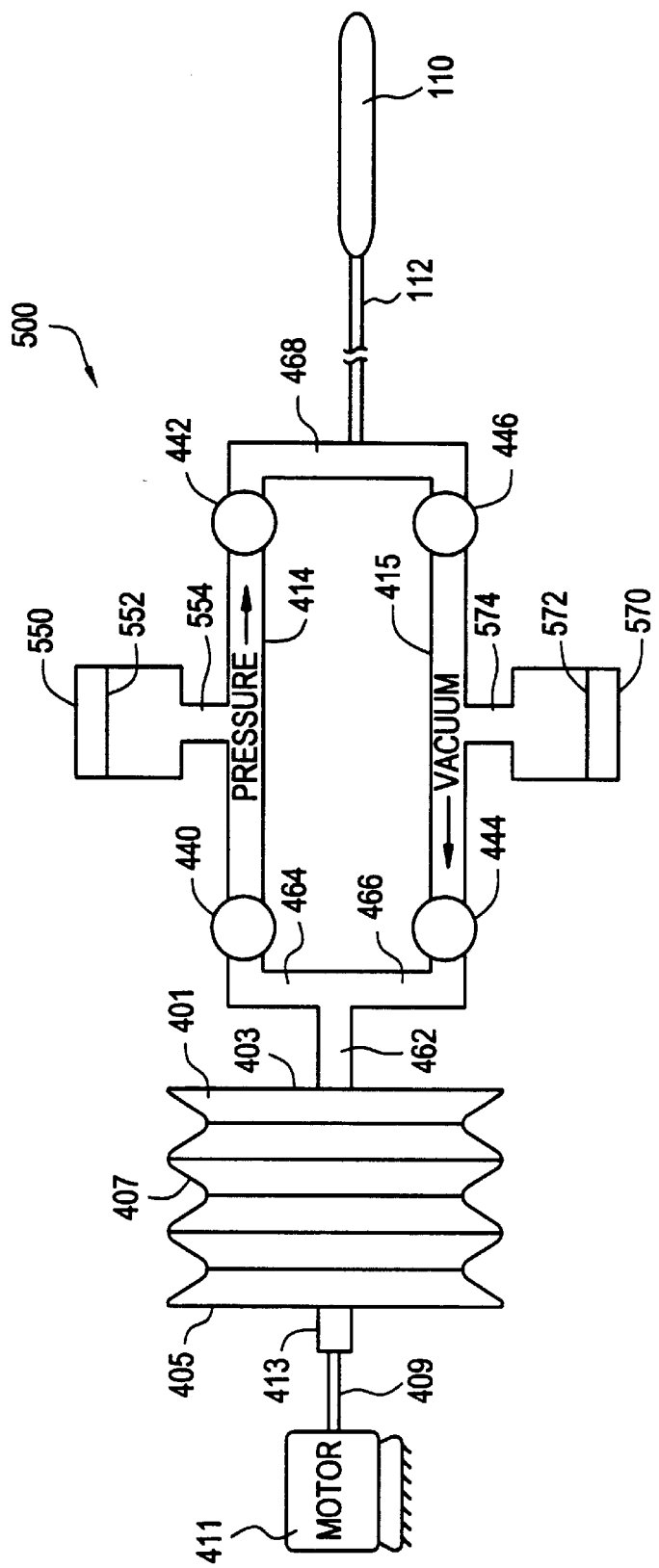
FIG. 7 is a highly schematic view showing a system for inflating and deflating an intra-aortic balloon in accordance with a fifth embodiment of the present invention.

A variant of intra-aortic balloon pump 400 is illustrated schematically in FIG. 7. In accordance with this variant, an intra-aortic balloon pump 500 includes a pressure accumulator 550 connected to extender 414 between valves 440 and 442, and a vacuum extender 570 connected to extender 415 between valves 444 and 446. Accumulators 550 and 570 may be similar to accumulator 250 described above, but do not need to bias their pistons or membranes in both a forward and backward direction toward a neutral position near the center thereof Rather, accumulator 550 may be a pressure accumulator in which piston or membrane 552 is biased only in a forward direction toward inlet/outlet port 554, such as, for example, by a mechanical force, such as from a spring, or by a gas force. On the other hand, accumulator 570 may be a vacuum accumulator in which piston or membrane 572 is biased only in a backward direction away from the inlet/outlet port 554. The biasing force in accumulator 570 may also be mechanical, such as by a spring, or through action of a trapped gas. Accumulator 550 will act similarly to accumulator 250 during the process of inflating balloon 110, and accumulator 570 will act similarly to accumulator 250 during the process of deflating balloon 110.

Thus, during the pre-inflation phase, opening valve 440 will cause helium to flow not only into extender 414, but also into accumulator 550, pushing piston 552 therein in a direction away from inlet/outlet port 554. Once back plate 405 of bellows 401 bottoms out in its fully forward position, valve 440 may be closed, trapping helium under pressure in extender 414 and accumulator 550. At this juncture, the controller may initiate a pre-deflation phase. That is, stepper motor 411 may be actuated so as to pull bellows backplate 405 rearward, increasing the volume of bellows 401 and creating a negative pressure therein. Since valves 440 and 444 are closed, bellows 401 is isolated from the remainder of the balloon pump, and no helium will flow out from extenders 414 or 415 into the bellows. Even as bellows 401 is expanding during a pre-deflation step, valve 442 may be opened to inflate balloon 110. As helium flows out from extender 414 and accumulator 550 to the balloon, the piston 552 in the accumulator will move forward to maintain the inflation pressure in extender 414 at a substantially constant level for at least a significant part of the inflation cycle. Preferably, accumulator 550 is designed with a volume sufficient to maintain the pressure in the extender at a substantially constant level during the entire inflation cycle.

The inflation cycle is continued until balloon 110 has reached the desired degree of inflation. This may occur when the passive portion of the system, i.e., extender 414, accumulator 550, extender portion 468, catheter 112 and balloon 110, has reached a state of equilibrium, at which point valve 442 is closed. Alternatively, based on a certain timing or on the measurement of conditions within balloon 110, valve 442 may be closed to terminate inflation before the passive portion of the system has reached equilibrium. In the event valve 442 is closed before equilibrium has been reached, helium at a greater positive pressure will be trapped in extender 414 and accumulator 550 than in situations where equilibrium is reached before valve 442 is closed. The higher the pressure of helium trapped between valves 440 and 442, the greater the pneumatic efficiency of the system.

As noted above, once valve 440 has been closed to conclude the pre-inflation phase, the controller may commence the pre-deflation phase by expanding the volume of bellows 401 to create a negative pressure therein. Subsequently, valve 444 may be opened, drawing helium out from extender 415 and accumulator 570, and drawing piston 572 therein outwardly toward inlet/outlet port 574. With valves 440 and 446 in a closed position, this procedure will have no impact on the helium pressure extant in extender 414, extender 468 or balloon 110, and therefore may be performed even as balloon 110 is being inflated. When bellows 401 reaches its fully expanded condition, valve 444 may be closed, trapping helium at a negative pressure in extender 415 and accumulator 570. With valve 444 closed, the controller may initiate a pre-inflation phase by actuating stepper motor 411 to compress bellows 401. This pre-inflation phase has no effect on the pressure in extenders 414 and 415 since valves 440 and 444 are closed. Independently of the pre-inflation phase, valve 446 may be opened to deflate balloon 110. As helium flows out from the balloon and into extender 415 and accumulator 570, the piston 572 in the accumulator will move rearwardly to maintain the deflation pressure in extender 415 at a substantially constant level for at least a significant portion of the deflation cycle. Preferably, accumulator 570 has a sufficient volume to maintain the pressure in the extender at a substantially constant level during the entire deflation cycle.

Deflation is continued until balloon 110 has reached the desired degree of deflation. This may occur either when the passive portion of the system has reached a state of equilibrium, at which point valve 446 is closed, or by closing valve 446 before equilibrium is reached based on a certain timing or certain measurement data.

Figure 8:
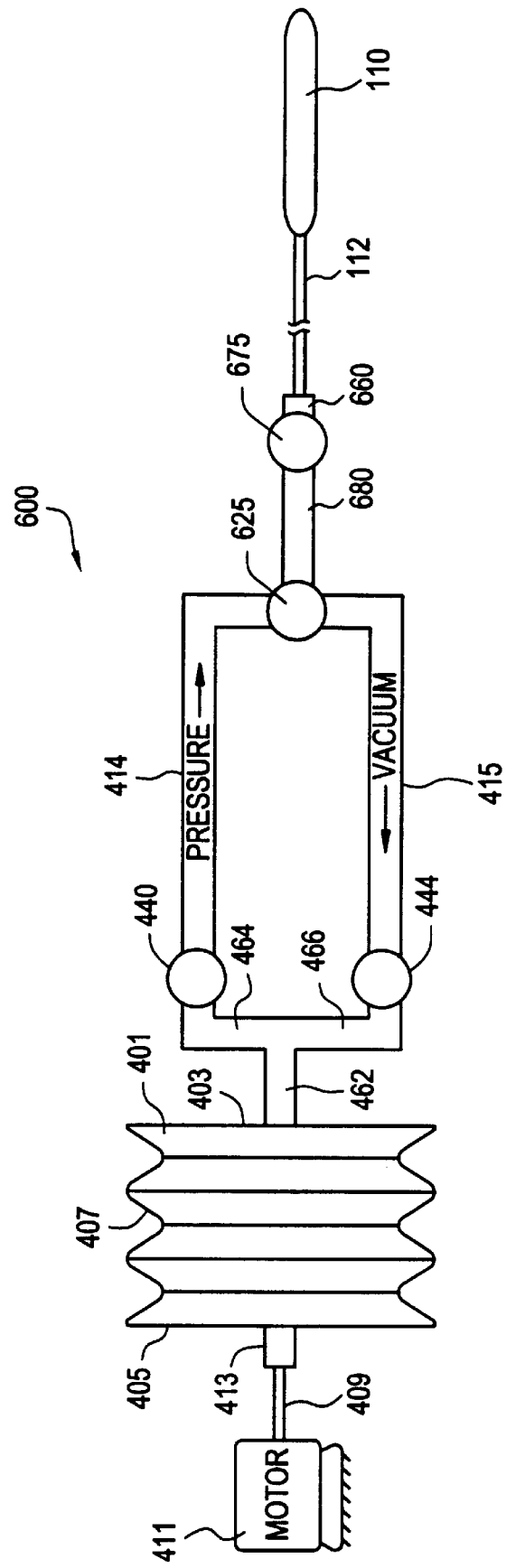
FIG. 8 is a highly schematic view showing a system for inflating and deflating an intra-aortic balloon in accordance with a sixth embodiment of the present invention.

A still further embodiment of an intra-aortic balloon pump 600 in accordance with the present invention is shown schematically in FIG. 8. Balloon pump 600 is similar to balloon pump 400 described above. However, rather than having a 2-way valve 442 at the end of extender 414 and a separate 2-way valve 446 at the end of extender 415, balloon pump 600 includes a single 2-way valve 625 to which the ends of extenders 414 and 415 are connected. Balloon pump 600 also includes a second 2-way valve 675 separated from valve 625 by an extender portion 680. Valve 675 may be positioned at the extreme end of extender portion 680 adjacent its connection to catheter 112, or in close proximity to the end of extender portion 680 such that only a short length of extender 660 is extant between valves 675 and catheter 112.

The pre-inflation phase using intra-aortic balloon pump 600 begins with balloon 110 in a fully deflated condition, bellows 401 in an expanded condition, valve 440 closed, valve 625 open to flow through extender 415, and valves 444 and 675 open. The controller may initially actuate valves 444 and 675 to close, trapping helium at negative pressure within extender 415 and extender portion 680. Stepper motor 411 may then be actuated to compress bellows 401, building up positive pressure therein. After a small delay, valve 440 may be opened and valve 625 may be switched to flow communication with extender 414. Little helium will move from the bellows into extender 414 during this pre-inflation phase, except that extender portion 680 will be filled with helium at positive pressure. No helium will flow into extender 415 because valve 444 is closed and valve 625 is in flow communication with extender 414 only. Since valve 675 remains in a closed position during this pre-inflation phase, no helium will flow from extender portion 680 into balloon 110. When inflation is desired, valve 675 may be opened, causing helium to flow from extender 414 and extender portion 680 into the balloon.

When balloon 110 has reached a desired degree of inflation, valves 440 and 675 may be closed, trapping helium at a positive pressure within extender 414 and extender portion 680. (It will be appreciated, of course, that valve 440 may be closed sooner should back plate 405 of bellows 401 reach its fully forward position before inflation has been completed.) Once valve 440 has been closed, a pre-deflation phase may be initiated by expanding the volume of bellows 401 so as to create a negative pressure therein. After a small delay, valve 444 may be opened and valve 625 may be switched to flow communication with extender 415, drawing helium out from extender 415 and extender portion 680 and into bellows 401. Little movement of helium will take place during this predeflation phase, except that extender portion 680 will be placed in a negative pressure condition. Since valve 675 remains closed during this pre-deflation phase, no deflation of balloon 110 will take place. To commence deflation, valve 675 may be opened, causing helium to flow out from balloon 110 and through extender portion 680 and extender 415 to bellows 401. No helium will flow into extender 414 since valve 440 is closed and valve 625 is positioned for flow communication with extender 415 only.

The present invention contemplates the use of the separate pressure and vacuum extenders, accumulators and valve arrangements described herein in combination with still other arrangements for the controlled inflation and deflation of balloon 110. Thus, for example, rather than isolator 118 or bellows 401, the inflation and deflation of balloon 110 may be effected by a system incorporating a piston reciprocally movable in a sleeve so that movement of the piston in a forward direction pushes gas into the extender and movement of the piston in the backward direction draws gas out from the extender. Inflation and deflation may also be effected by a system incorporating a turbine rotatably mounted between a fixed volume chamber and the extender so that rotation of the turbine in one direction draws gas from the chamber and pushes it into the extender, and rotation of the turbine in the opposite direction draws gas away from the extender and pushes it into the chamber. A still further system may include a pressure source, a vacuum source and a vent port mounted through solenoid valves directly to the extender or extenders, such that operation of each solenoid valve for a predetermined length of time would produce the desired pressure in the respective extenders. Any arrangement for effecting the inflation and deflation of balloon 110 other than those described above is also contemplated herein.

Although the invention herein has been described with reference to particular embodiments, it is to be understood that these embodiments are merely illustrative of the principles and applications of the present invention. It is therefore to be understood that numerous modifications may be made to the illustrative embodiments. For example, either one or two accumulators, as described in connection with intra-aortic balloon pumps 200 and 500, may be used with the other embodiments described herein. Still other arrangements may be devised without departing from the spirit and scope of the present invention as set forth in the appended claims.

What is claimed is:

1. A method for inflating and deflating a medical device, said medical device being connected to a conduit including a tubular extender portion having a relatively large diameter lumen and a tubular catheter portion having a relative small diameter lumen connected in series so that one end of said catheter portion is connected in flow communication to one end of said extender portion and another end of said catheter portion is connected in flow communication to said medical device, said method comprising applying a working gas to said extender portion to develop an inflation pressure therein while interrupting flow communication between said extender portion and said catheter portion, whereby said working gas is prevented from flowing into said catheter portion and said medical device;

establishing flow communication between said extender portion and said catheter portion, whereby said working gas flows from said extender portion through said catheter portion to said medical device to substantially fully inflate the medical device to a working pressure lower than said inflation pressure; and reducing the pressure in said extender portion to a deflation pressure less than said working pressure, whereby said working gas flows from said medical device through said catheter portion to said extender portion to substantially fully deflate said medical device.

2. A method for inflating and deflating a medical device, said medical device being connected to a conduit including a tubular extender portion having a relatively large diameter lumen and a tubular catheter portion having a relatively small diameter lumen connected in series so that one end of said catheter portion is connected in flow communication to one end of said extender portion and another end of said catheter portion is connected in flow communication to said medical device, said method comprising applying a working gas to said extender portion to develop an inflation pressure therein, whereby said working gas flows from said extender portion through said catheter portion to said medical device to substantially fully inflate said medical device to a working pressure;

removing said working gas from said extender portion to develop a deflation pressure therein while interrupting flow communication between said extender portion and said catheter portion, whereby said working gas is prevented from flowing out from said catheter portion and said medical device, said deflation pressure being less than said working pressure; and establishing flow communication between said extender portion and said catheter portion, whereby said working gas flows from said medical device through said catheter portion to said extender portion to substantially fully deflate said medical device.

3. A method for inflating and deflating a medical device, said medical device being connected to a conduit including a tubular extender portion having a relatively large diameter lumen and a tubular catheter portion having a relatively small diameter lumen connected in series so that one end of said catheter portion is connected in flow communication to one end of said extender portion and another end of said catheter portion is connected in flow communication to said medical device, said method comprising applying a working gas to said extender portion to develop an inflation pressure therein while interrupting flow communication between said extender portion and said catheter portion, whereby said working gas is prevented from flowing into said catheter portion and said medical device;

establishing a first flow communication between said extender portion and said catheter portion, whereby said working gas flows from said extender portion through said catheter portion to said medical device to substantially fully inflate said medical device to a working pressure lower than said inflation pressure;

removing said working gas from said extender portion to develop a deflation pressure therein while interrupting said first flow communication between said extender portion and said catheter portion, whereby said working gas is prevented from flowing out from said catheter portion and said medical device, said deflation pressure being less than said working pressure; and establishing a second flow communication between said extender portion and said catheter portion, whereby said working gas flows from said medical device through said catheter portion to said extender portion to substantially fully deflate said medical device.

4. The method as claimed in claim 3, further comprising the step of providing a hollow element at a free end of said extender portion, wherein said step of removing said working gas from said extender portion includes the steps of supplying said working gas to said hollow element at a pressure less than said working pressure, and establishing flow communication between said hollow element and said extender portion, whereby said working gas flows from said extender portion into said hollow element.

5. The method as claimed in claim 4, wherein said step of establishing said second flow communication between said extender portion and said catheter portion occurs while there is flow communication between said hollow element and said extender portion.

6. The method as claimed in claim 3, further comprising the step of providing a hollow element at a free end of said extender portion, wherein said step of applying said working gas to said extender portion includes the steps of supplying said working gas to said hollow element at a pressure greater than the pressure prevailing in said extender portion, and establishing a first flow communication between said hollow element and said extender portion, whereby said working gas flows from said hollow element into said extender portion.

7. The method as claimed in claim 6, wherein said step of establishing said first flow communication between said hollow element and said extender portion occurs after said step of supplying said working gas to said hollow element.

8. The method as claimed in claim 6, wherein said step of removing said working gas from said extender portion includes the steps of supplying said working gas to said hollow element at a pressure less than said working pressure, and establishing a second flow communication between said hollow element and said extender portion, whereby said working gas flows from said extender portion into said hollow element.

9. The method as claimed in claim 8, wherein said step of establishing said second flow communication between said hollow element and said extender portion occurs after said step of supplying said working gas to said hollow element at a pressure less than said working pressure.

10. The method as claimed in claim 6, wherein said step of establishing said first flow communication between said extender portion and said catheter portion occurs while there is flow communication between said hollow element and said extender portion.

11. The method as claimed in claim 10, further comprising the steps of interrupting said first flow communication between said hollow element and said extender portion while there is flow communication between said extender portion and said catheter portion, and supplying said working gas to said hollow element at a pressure less than said working pressure.

12. The method as claimed in claim 11, wherein said step of removing said working gas from said extender portion includes the step of establishing a second flow communication between said hollow element and said extender portion, whereby said working gas flows from said extender portion into said hollow element.

13. The method as claimed in claim 6, further comprising the step of interrupting said first flow communication between said hollow element and said extender portion after said inflation pressure has been developed in said extender portion and prior to said step of establishing said first flow communication between said extender portion and said catheter portion.

14. The method as claimed in claim 13, further comprising the step of supplying said working gas to said hollow element at a pressure less than said working pressure after said first flow communication between said hollow element and said extender portion has been interrupted, whereby said working gas does not flow from said extender portion to said hollow element.

15. The method as claimed in claim 14, wherein said step of removing said working gas from said extender portion includes the step of establishing a second flow communication between said hollow element and said extender portion.

16. The method as claimed in claim 15, further comprising the step of interrupting said second flow communication between said hollow element and said extender portion after said deflation pressure has been developed in said extender portion and prior to said step of establishing said second flow communication between said extender portion and said catheter portion.

17. The method as claimed in claim 13, further comprising the step of providing a variable volume reservoir in flow communication with said extender portion, wherein said step of applying said working gas to said extender portion develops said inflation pressure in both said variable volume reservoir and said extender portion.

18. The method as claimed in claim 17, wherein, when said first flow communication is established between said extender portion and said catheter portion and said working gas flows from said extender portion through said catheter portion to said medical device, said working gas flows from said variable volume reservoir to said extender portion.

19. The method as claimed in claim 18, wherein said step of removing said working gas from said extender portion develops said deflation pressure in both said variable volume reservoir and said extender portion.

20. The method as claimed in claim 19, wherein, when said second flow communication is established between said extender portion and said catheter portion and said working gas flows from said medical device through said catheter portion to said extender portion, said working gas flows from said extender portion to said variable volume reservoir.

21. The method as claimed in claim 13, further comprising the step of providing a variable volume reservoir in flow communication with said extender portion, wherein said step of removing said working gas from said extender portion develops said deflation pressure in both said variable volume reservoir and said extender portion.

22. The method as claimed in claim 21, wherein, when said second flow communication is established between said extender portion and said catheter portion and said working gas flows from said medical device through said catheter portion to said extender portion, said working gas flows from said extender portion to said variable volume reservoir.

* * * * *